United States Patent [19]

Sones et al.

[11] Patent Number: 4,817,123

[45] Date of Patent: Mar. 28, 1989

[54] DIGITAL RADIOGRAPHY DETECTOR RESOLUTION IMPROVEMENT

[75] Inventors: Richard A. Sones, Cleveland Heights; Mike M. Tesic, Cleveland, both of Ohio

[73] Assignee: Picker International, Cleveland, Ohio

[21] Appl. No.: 898,762

[22] Filed: Aug. 14, 1986

Related U.S. Application Data

[63] Continuation of Ser. No. 653,955, Sep. 21, 1984, abandoned.

[51] Int. Cl.$^4$ ................................................ H05G 1/38
[52] U.S. Cl. ..................................... 378/98; 378/146; 378/62; 250/369
[58] Field of Search .................... 378/19, 95, 98, 146, 378/62; 250/369

[56] References Cited

U.S. PATENT DOCUMENTS

| | | |
|---|---|---|
| 2,776,377 | 1/1957 | Anger . |
| 3,717,762 | 2/1973 | Grenier et al. . |
| 3,970,853 | 7/1976 | Kuhl et al. . |
| 4,029,963 | 6/1977 | Alvarez et al. ........................ 378/5 |
| 4,160,167 | 7/1979 | Weiss et al. . |
| 4,176,280 | 11/1979 | Greschat et al. . |
| 4,203,037 | 5/1980 | Gur et al. ............................ 378/62 |
| 4,242,583 | 12/1980 | Annis et al. . |
| 4,284,891 | 8/1981 | Pergrale et al. . |
| 4,366,574 | 12/1982 | Hill . |
| 4,383,327 | 5/1983 | Kruger . |
| 4,398,302 | 8/1983 | Pfeiler . |
| 4,404,591 | 9/1983 | Bonar . |
| 4,414,682 | 11/1983 | Annis et al. . |
| 4,429,226 | 1/1984 | Inbar . |
| 4,434,369 | 2/1984 | Metal . |
| 4,503,332 | 5/1985 | Annis .................................. 378/146 |
| 4,511,799 | 4/1985 | Bjorkholm ............................ 378/5 |
| 4,626,688 | 12/1986 | Barnes ................................ 250/367 |
| 4,642,464 | 2/1987 | Mullani ............................ 250/363 S |

FOREIGN PATENT DOCUMENTS

| | | |
|---|---|---|
| 0089148 | 3/1983 | European Pat. Off. . |
| 01155125 | 11/1983 | European Pat. Off. . |
| 0206996 | 12/1983 | Japan ................................ 378/19 |

OTHER PUBLICATIONS

Electronic Imaging, Aug. 1984, "Xerox CCD".

Primary Examiner—Craig E. Church
Assistant Examiner—John C. Freeman
Attorney, Agent, or Firm—Watts, Hoffman Fisher & Heinke

[57] ABSTRACT

A digital radiographic system and method is disclosed having improved detector resolution. The system includes an X-ray source and a spaced detector assembly having several staggered columns of uniform square detector elements. The detector elements are thus arranged in interspersed rows with the center-to-center spacing between successive members of each row being about twice the lateral dimension of each square element. In response to incident X-radiation, each detector element produces an electrical charge signal indicative of the radiation. Power means actuates the source to propagate X-ray energy in a beam along a path toward the detector assembly, in which path a subject may be interposed for examination. Mechanism is provided for scanning the detector assembly, synchronously and in alignment with the X-ray beam, relative to a subject. The relative scanning motion is perpendicular to the columns of detector elements. Time delay and integrate circuitry is provided, separate from but coupled to the detector elements. Detector element electrical signals are sampled at successive increments of scanning motion equal to half the width of a detector element. Respective delay circuitry built into the time delay and integrate circuitry delays element output signals differently as a function of detector element spacing and sampling frequency, in order to superimpose data for each respective image pixel and to present all signals relating to each respective pixel simultaneously to a summing output for imaging.

28 Claims, 5 Drawing Sheets

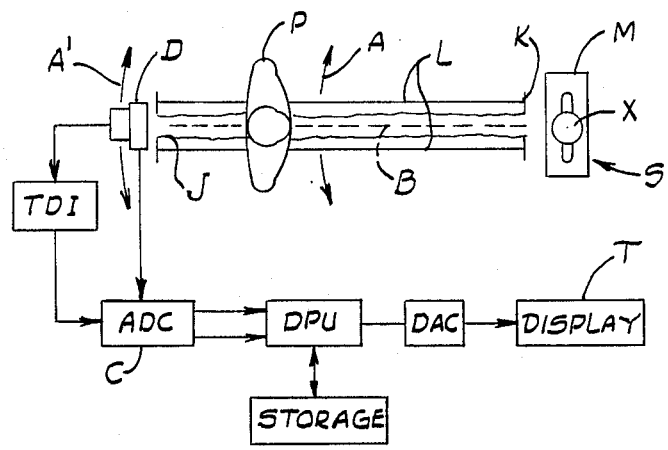
Fig. 2
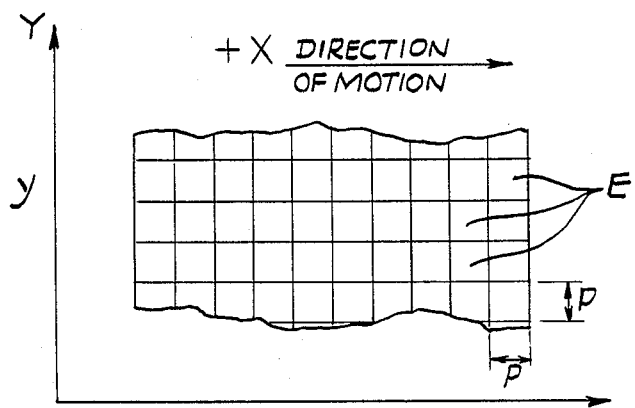
Fig. 3
(PRIOR ART)
Fig. 4
(PRIOR ART)

TIME DELAY INTEGRATION IN CONJUNCTION
WITH STAGGERED MULTI-LINEAR DETECTOR ARRAY

DIGITAL RADIOGRAPHY DETECTOR RESOLUTION IMPROVEMENT

This application is a continuation of application Ser. No. 653,955, filed Sept. 21, 1984, now abandoned, which corresponds to European patent application Ser. No. EPNO. 0115125-A1 published on Aug. 8, 1984.

TECHNICAL FIELD

This invention relates to the field of medical diagnostic imaging and more particularly to a digital radiography system having improved detector resolution. This invention deals with a detector geometry and shift-and-add imaging circuitry for realizing such improved resolution.

BACKGROUND ART

Radiography is a long known medical diagnostic imaging technique.

In a conventional radiography system, an X-ray source is actuated to direct a divergent area beam of X-rays through a patient. A cassette containing an X-ray sensitive phosphor screen and light and X-ray sensitive film is positioned in the X-ray path on the side of the patient opposite the source. X-radiation passing through the patient's body is attenuated to produce a shadow image of a portion of the patient through which the X-rays pass.

More recently, digital radiographic techniques and systems have been developed. In digital radiography, the source directs X-radiation through a patient's body to a detector assembly located in the beam path beyond the patient. The detector produces electrical signals defining the radiation pattern emergent from the patient. These signals are then processed to yield a visual display of the image.

The detector assembly includes an elongated array of individual discrete detector elements. Each detector element responds to incident X-radiation to produce an analog electrical charge signal indicative of such radiation. These analog electrical signals represent the radiation pattern or image emergent from the patient's body and incident on the detector array.

The analog signals are sampled and processed by imaging circuitry, primarily to improve their signal to noise ratio, and are subsequently digitized.

The digital signals are fed to a digital data processing unit (DPU). The data processing unit records and/or processes and enhances the digital data.

A display unit responds to appropriate digital data representing the image to convert the digital information back into analog form and to produce a visual display of the patient's internal body structure derived from the acquired image pattern of radiation.

The display unit can be coupled directly to the digital data processing unit for substantially real time imaging, or can be fed stored digital data from digital storage means such as tapes or disks representing patient images produced from earlier studies.

Digital radiography includes techniques in which a thin spread beam of X-radiation is used. In practice of this technique, often called "scan (or slit) projection radiography" (SPR), the spread beam is scanned across the patient, or the patient is movably interposed between the spread beam X-ray source and the detector assembly, the detector being maintained in continuous alignment with the beam. The relative movement effected between the source-detector arrangement and the patient's body scans a large portion of the body.

Discrete element detectors have been proposed comprising a single line of detector elements. Other proposals have included rectangular detector arrays of square detector elements.

Details of certain aspects of digital radiography systems such as described here are set forth in the following publications, hereby expressly incorporated by reference:

Mattson, R. A., et al, "Design and Physical Characteristics of a Digital Chest Unit", S.P.I.E. Volume 314, *Digital Radiography* (1981).

Arnold, B. A. et al "Digital Radiography: An Overview" *Proc. of S.P.I.E.* Volume 273, March 1981;

Kruger, R. A. et al "A Digital Video Image Processor for Real Time X-Ray Subtraction Imaging" *Optical Engineering* Volume 17, No. 6 (1978);

U.S. patent application Ser. No. 444,605, filed Nov. 26, 1982 by Gary L. Barnes and entitled "Split Energy Level Radiation Detection" which corresponds to European patent application Ser. No. EP-0115125-A1 published on August 8, 1984;

U.S. patent application No. 542,384, filed Oct. 17, 1983 by Mattson, et al entitled "Improving Signal Characteristics in Digital Scan Projection Radiography".

An alternate proposal to the detector element array described above is a detector array consisting of two side by side vertical columns of square detector elements. One of the columns, however, is slightly vertically displaced, or offset, with respect to the other by a distance equal to one half the height of a single detector element. Such a configuration is described in the above incorporated application by Barnes.

It has also been proposed, where the detector array comprises a rectangular array of square detector elements, to improve the signal to noise ratio of the information developed by the detector, by the use of time delay and integrate (TDI) circuitry. An embodiment of such a proposed system is described in U.S. Pat. No. 4,383,327, issued May 10, 1983 to Kruger, which is hereby incorporated by reference. Such proposed TDI systems employ sampling at regular intervals of detector motion, and motion-synchronous shifting and adding of individual detector-produced analog charge signals. In such systems, the TDI circuitry can be integral with the detector elements.

Important advantages of scanning slit radiography are excellent scatter rejection and compatibility with digital image sensors. A significant disadvantage of such systems is the requirement of heavy X-ray tube loading that results from inefficient utilization of the X-ray output. This inefficiency arises from the aperture width which defines the spread beam subtending only a small solid angle at the focal spot of the X-ray tube.

To alleviate this disadvantage, it has been proposed to use a spread beam which is as thick as possible without unduly compromising the inherent good scatter rejection of such systems employing thin beams. See the above incorporated patent application by Mattson et al. As the spread beam is widened, however, the use of a rectangular detector array becomes more difficult. Such difficulty arises because, as the spread beam is thickened, more detector elements are needed, data rates become high and accordingly more difficult to handle, and TDI techniques must be used for shifting and adding data synchronously with scan motion so that data pertaining to each image portion, or "pixel" are properly superimposed to avoid image blurring.

Where time delay and integrate shifting and adding circuitry is employed, the detector element output signals are sampled at successive increments of detector movement equal to the length of a side of a single detector element. For reasons explained in more detail below, the spatial resolution of a rectangular detector array when used with TDI as described above is poorer than the maximum inherently obtainable resolution.

To facilitate understanding of both the prior art and the present invention, certain information and definitions relating to imaging optics are useful.

The ability of any optical element or system to resolve images is often described in terms of its "modulation transfer function" (MTF). Normally, the ability of an optical system to resolve a portion of an image decreases as the fineness of detail of the image portion (the number of lines per unit distance) increases. The number of lines per unit distance is frequently expressed as "line pairs per millimeter", and is known as the "spatial frequency" of the image portion of interest. The degradation of resolution as detail increases is manifested as a reduction in the contrast between the light and dark areas of the image portion. MTF is the function of contrast ratio versus the spatial frequency.

A rectangular detector element has an MTF in each of the x and y co-ordinates of its energy receiving face. In a square detector element $MTF_x = MTF_y$, and both functions can be demonstrated to be represented by the expression sinc (pf), where p is the length of one side of the square element receiving face, f is the spatial frequency sought to be imaged, and the sinc function is defined as sinc $x = \sin(\pi x)/(\pi x)$ According to the above relationship, the x and y MTF's each are first reduced to 0 when the spatial frequency increases to $f = 1/p$. This first zero is generally taken as representing the maximum spatial frequency (detail) which a square detector element can reliably image.

This phenonemon is one limiting factor on the resolving capability of any square detector, and is dependent upon its size, or "aperture". This parameter is referred to as the "aperture cutoff frequency".

A detector element is also limited by another resolution constraint known as the "Nyquist frequency". The Nyquist frequency is a spatial frequency above which the detector element cannot resolve separate lines. Rather than being a function of the detector size, however, the Nyquist frequency is related to the incremental distance at which successive samplings of the detector element output signal occur. The Nyquist cutoff frequency is relevant since the use of TDI circuitry requires repeated detector output samplings.

Where a row of square detectors, extending in the x coordinate in a rectangular array, is sampled once for each successive element width increment, (sampling distance) (as in the prior art) it can be shown, as set forth in publications referenced below, that the Nyquist frequency is only 1/(2p), along both coordinate axes. Therefore, in such a rectangular array, sampled as described, the Nyquist frequency is twice as limiting to resolution as is the aperture cutoff. Thus, the spatial frequency at which the resolving capability disappears under the Nyquist criterion is only half the frequency at which the resolving capability disappears under the aperture cutoff frequency criterion.

This means that, where a moving rectangular array of square elements is employed, and a row of elements is sampled only at successive increments of one detector width, the spatial resolution of such a detector is poorer than the maximum obtainable, as dictated by the detector element size, or aperture, under the aperture cutoff criterion. Also, aliasing artifacts will be present in an image derived from such a detector.

The Nyquist criterion is also applicable in the y coordinate of a rectangular array. In the y direction, the equivalent sampling distance between adjacent rows of square elements is the length p of one side of an element.

The following publications are hereby expressely incorporated by reference, for the assistance of those not conversant with this art, which are explanatory of the theory relating to these conclusions:

Sones, R. A., et al "A Method to Measure the MTF of Digital X-ray Systems" *Medical Physics* 11(2), March/April 1984, pages 166–171; Giger, M. L. et al "Investigation of Basic Imaging Properties in Digital Radiography: Modulation Transfer Function" *Medical Physics* 11(3) May/June 1984, at pages 287–295.

It has been seen that, where a rectangular array of square elements is sampled only once for each successive element width of motion, the system fails to take full advantage of the resolving power of the elements as dictated by their size.

The same conclusion applies to resolution in the y coordinate of the rectangular array. This is because the effective sampling distance between adjacent rows of the arrays is defined as p, the same as in the x direction.

Therefore, a rectangular array, sampled at incremental distance p fails to take full advantage of its inherent resolving power, in either the x or y coordinate.

It has been proposed that the use of an offset array, having only two columns, might be used to improve (reduce) the effective sampling distance increment in the y direction. This, however, is only a partial improvement, since it does not afford any reduction in the sampling distance in the x coordinate.

Moreover, since such detectors have only two columns of elements, and the detector array scans perpendicular to the columns, such an array has not been used in conjunction with TDI imaging circuitry. Thus, the signal-enhancing benefits of such circuitry have not been useful in conjunction with any known staggered, or offset, array.

It is an object of this invention to take maximum advantage of the resolving capabilities of the individual detector elements of the detector array, as defined by the aperture cutoff criterion, by eliminating the Nyquist frequency restriction in both x and y coordinates, while maintaining the full benefits of the use of time delay and integrate circuitry for enhancing the signal to noise ratio of the data acquired by the detector array.

DISCLOSURE OF INVENTION

The disadvantages of the prior art explained above are reduced or eliminated by a digital radiography system and method incorporating improved detector array geometry and novel time delay and integrate circuitry associated therewith, employing an improved operational sequence particularly adapted for use with the new detector geometry.

A digital radiography system embodying the present invention includes a radiation source and a detector array spaced sufficiently from the source to accommodate the placement of a patient between the source and the detector. Mechanism is provided for scanning the detector array relative to a patient while aligned with the radiation source. Power means is employed for actuating the source to direct radiation through the patient and toward the detector array during scanning. The array comprises a number of detector elements each responsive to incident radiation to produce electrical signals indicative of the radiaton. Circuitry coupled to the detector array responds to these signals to generate an image depicting internal structure of the patient as evidenced by a radiation pattern emergent from the patient and incident on the detector array.

The detector array comprises a plurality of individual detector elements, arranged in a pattern of staggered columns, the array being scanned in a direction substantially perpendicular to the columns.

The staggered nature of the detector element columns geometrically reduces the effective sampling distance between adjacent rows of detector elements to an amount equal to ½ the dimension of a single detector element taken in a direction along the columns. This phenomenon results because of a specific aspect of the invention wherein each staggered column of elements is displaced from adjacent columns by an amount equal to ½ the dimension of a single detector element along the column. This configuration results in a pattern wherein adjacent rows of detector elements are partially interspersed with one another.

This geometry improves the resolving capability of the detector array in the y direction (parallel to the columns) to the limit of its resolving power as dictated by the aperture cutoff frequency determined by element size. The geometry modifies the Nyquist frequency of the detector in the y direction to a value which is substantially coincident with the aperture cutoff frequency, rather than permitting a Nyquist frequency more limiting in resolution than the aperture cutoff criterion.

Resolution of the detector in the x direction (perpendicular to the columns) is improved by employment of novel time delay and integrate circuitry and by provision for its operation in a novel sequence. More specifically, the TDI circuitry samples detector element outputs at successive increments of detector motion equal to ½ the width of a single detector element in a direction perpendicular to the column, i.e., parallel to the detector element rows. This actual reduction in sampling distance improves the Nyquist frequency in the x direction, rendering it substantially equal to the aperture cutoff frequency, so that the Nyquist frequency does not limit resolution to a level poorer than that permitted by the aperture cutoff limitation.

A more specific feature of the invention resides in the use of individual detector elements having a substantially uniform square cross-section. The use of such square elements (as opposed to circular elements, for example) facilitates obtaining the maximum radiation sensitive surface area with respect to a given overall detector assembly size.

An aspect of the TDI circuitry of this invention resides in that the circuitry must be separate from, rather than integral with, the individual detector elements. This aspect permits the interposition of different delay circuitry in the respective outputs of the individual detector elements.

The provision of individual respective delay in the outputs from the several detector elements facilitates obtaining the benefits of both the staggered nature of the array geometry and of the employment of sampling at successive detector element half width increments.

These benefits are implemented by a more specific feature of the invention, wherein delay circuitry is provided such that output signals from each member of a detector element row are delayed, with respect to those of the immediately preceding detector element, as a function of the x direction sampling distance and by the degree of separation of the elements of the row resulting from the interspersion of adjacent rows. This technique enables TDI circuitry to transmit simultaneously to an output all detector element signals pertaining to a particular image pixel.

These and other features and aspects of this invention will become apparent with reference to the following specific description, and to the drawings, in which:

BRIEF DESCRIPTION OF THE DRAWINGS

FIG. 2 is a plan view, shown partially in graphical and partially in block form, of a digital radiography system incorporating the present invention;

FIG. 3 is an elevational view, partially broken away, illustrating a component of a prior art digital radiography system;

FIG. 4 is a graphical illustration of an operative sequence associated with use of the component illustrated in FIG. 3;

BEST MODE FOR CARRYING OUT THE INVENTION

Figure 1:
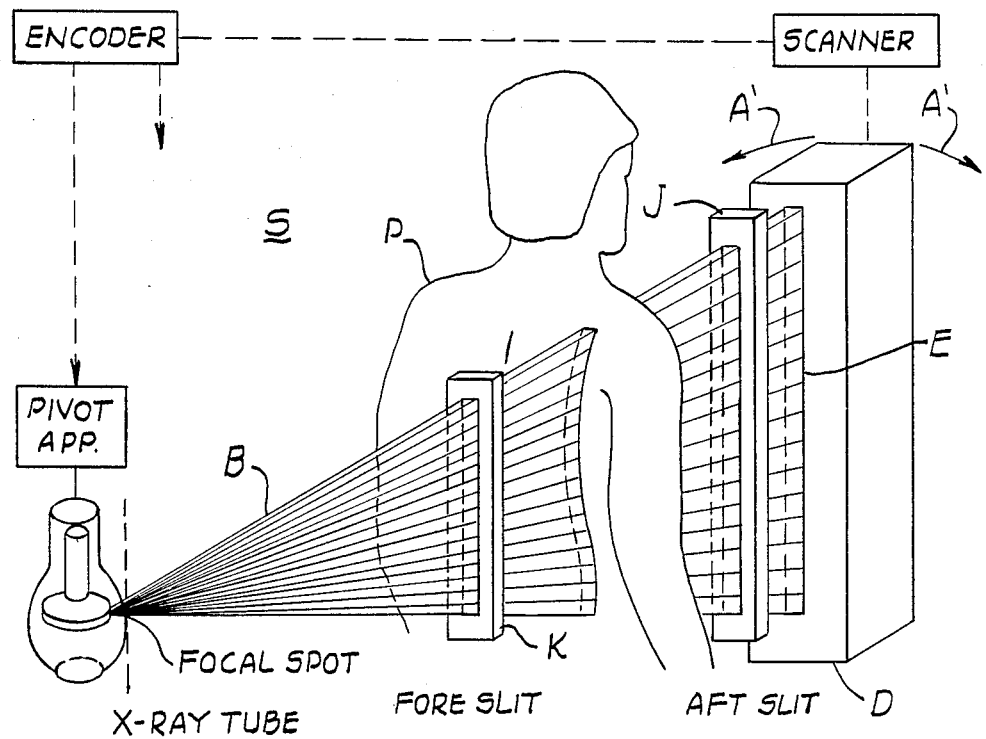
FIG. 1 is a perspective view of a digital radiography system incorporating the present invention.

FIGS. 1 and 2 illustrate a slit projection type of digital radiography system S in which the present invention is incorporated. The system S scans an X-ray spread beam approximately 1 to 2 centimeters in thickness about a vertical axis across a patient's chest and detects a pattern of X-rays emergent from the patient's body. Information represented by the detected X-rays is processed and displayed to illustrate a representation of an image of the patient's internal body structure or condition.

More specifically, the system S includes an X-ray source X affixed to mounting structure M for projecting the spread beam B of X-rays through the body of a patient P, to strike an aligned detector assembly D comprising a plurality of detector elements. The spread beam B is confined by a forward slit K to a substantially vertical plane. The detector assembly D comprises a generally vertically elongated staggered array of individual detector elements V (described in more detail below) and is aligned with the vertical plane defined by the spread beam B. An aft slit J attached to the detector assembly D serves to further define the spread beam B.

The X-ray source X is mounted on the structure M to rotate about a vertical axis, defined in FIG. 2 as extending into the plane of the paper. Mechanical linkage L couples the X-ray tube X to the detector array D and slits K and J and causes the detector array to scan behind the patient's body along an arcuate path defined by the arrows A, A' in order to maintain the detector assembly D aligned with the beam B throughout the scanning rotative motion of the beam.

The embodiment of the scanning mechanism is not to be limited to fixed or rigid mechanical linkage connecting the elements to be moved. Servo control and associated power drive apparatus embodiments can also be adapted by those of skill in the art to accomplish the desired scanning.

In accordance with another aspect of this embodiment, the X-ray tube X can also be pivoted about its focal spot, to maintain the beam B aligned with the scanning detector.

The X-ray source X is controlled by power means to emit the spread beam B as either a continuous X-ray beam or a rapid succession of X-ray pulses. The X-ray tube X and the detector assembly D synchronously scan, about a vertical axis, across the patient from one side of his body to the other. Analog detector outputs from each of the detector elements are periodically sampled. Each sampling produces analog signals representing a portion of image information. Over the course of the scan from one side to the other side, signals are developed describing a plurality of image lines, which together constitute an area image of the patient's internal body structure.

The analog signals produced by the detector assembly are provided to an analog to digital converter C which digitizes the outputs and feeds them to a digital processing and receiving unit DPU. The DPU processes these digitized output signals to construct a digital representation of an image of the patient's internal body structure scanned by the X-ray beam B, on a pixel-by-pixel basis. Digital signals from the DPU are converted to analog form by way of a digital to analog converter DAC, and fed to a display unit T, which, in response, produces an image in visual form corresponding to the image representing signals from the DPU.

Optionally, digital storage means can be provided in conjunction with the DPU in order to digitally store the image representations for future use. In such event, the digitally stored signals can be later played through the DPU, converted to analog form, and their corresponding images then displayed.

Coupled to each of the elements E (see FIG. 3) of the detector assembly D is time delay and integrate circuitry TDI. The time delay and integrate circuitry operates to shift and add analog signals from the detector elements E to produce other analog signals representing the data from the detector elements E possessing an improved signal-to-noise ratio. As pointed out above, a form of prior art TDI circuitry employed in digital radiography is described in the above incorporated Kruger patent.

A significant aspect of the present invention involves the configuration of the array of detector elements, and improvements in the structure and mode of operation of the TDI circuitry associated therewith. Understanding of the present invention is facilitated, however, by an explanation of the prior art detector configuration and corresponding sampling circuitry operation of the prior art.

The shifting and adding required for a prior art rectangular matrix of square detector elements (FIG. 3) is illustrated in FIG. 4. From the frame of reference of a patient, the detector array moves, to the right as shown in FIG. 3, at a constant speed v in the x direction. From the frame of reference of the detector array D, the patient moves in the $-x$ direction with speed $-v$.

Each of the detector elements (as shown at E in FIG. 3, for example) integrates the X-ray signal received, represented as accumulated electric charge, until it is sampled. If the detector elements are sampled every t seconds, in the patient's reference, the sampling distance d (in the x direction) is defined by the equation $d = vt$.

Consider a single row of ten detector elements extending in the x direction, as shown in FIG. 4. Let the expression $s(j,k)$ represent the charge accumulated at the k-th sampling of the j-th detector element, where the elements are numbered from right to left and j ranges from 0 to 9. Assume that the sampling is adjusted so that d is the same as the detector element center-to-center spacing p (the "pitch").

Consider the patient "pixel" located in alignment with the element 0 at sample 0. This pixel will be facing element 1 at sample 1, element 2 at sample 2, and so on. Hence the final value Q of the charge signal ultimately shifted from element 9, representing the X-ray value of the pixel in question, is given by the expression:

$$Q = s(0,0) + s(1,1) + \ldots + s(9,9). \qquad \text{(Eq. 1)}$$

Those of skill in the art will recognize that this equation describes a shift-and-add sequence. Time delay and integration (TDI) utilizing CCD (charge coupled device) analog shift registers is known to be appropriately suited to perform this shift-and-add sequence in the analog domain, as described in the above incorporated Kruger patent.

The prior art detector illustrated in FIG. 3 comprises a rectangular matrix of square detector elements having sides of length p. The spatial frequency response of this detector is the product of the x and y responses, i.e.:

$$\text{MTF} = (\text{MTFx})(\text{MTFy}) \qquad \text{(Equation 2)}$$

Also $$\text{MTFx} = \text{MTFy} = \text{sinc}(pf), \qquad \text{(Equation 3)}$$

where f is the spatial frequency. The x and y modulation transfer functions each have their first zero at $f = 1/p$. This is referred to here as the aperture cutoff frequency.

In the y direction, the sampling distance is simply the detector element pitch p.

In the x direction, the sampling distance d depends upon the sample interval t. In such prior art TDI applications, t must be chosen so that d equals p, as in the above example. The Nyquist frequency due to sampling is then $1/(2p)$ in both directions. Therefore, the Nyquist frequency is only half the detector aperture cutoff frequency. This means that the spatial resolution of the detector, in this prior art example, is poorer than that dictated by the detector element aperture, and aliasing artifacts will be present in an image derived from such a detector as explained above. Note that the pixel pitch (sampling pitch) is the same as the detector element pitch P.

The facts and theory described in connection with above prior art are within the scope of knowledge of one of ordinary skill in this art. For the benefit of those, however, who may not be conversant with the relevant art, the principles involved in the foregoing analysis are explained in the following publications, each of which is hereby expressly incorporated by reference:

Giger, M. L., et al "Investigation of Basic Imaging Properties in Digital Radiography: Modulation Transfer Function" *Medical Physics* 11(3) May/June 1984, at pages 287-295;

"A Method to Measure the MTF of Digital X-Ray Systems" Sones, R. A. et al *Medical Physics* 11(2) March/April 1984 at pages 166-172;

Goodman, J. W. "Introduction to Fourier Optics", McGraw-Hill 1968, at pages 21-25;

Newton, J. H. et al, "Radiology of the Skull and Brain", Technical Aspects of Computed Tomography, Volume 5, pp. 3931, 3958.

The present invention eliminates the discrepancy in resolving power of the detector between the inherent detector element aperture cutoff and the Nyquist frequency restriction. The present invention enables obtaining the maximum theoretical resolution inherently possible within the aperture cutoff limitation on resolution. This advantage is obtained consistent with full maintenance of the advantages of time delay and integration circuitry.

Figure 5:
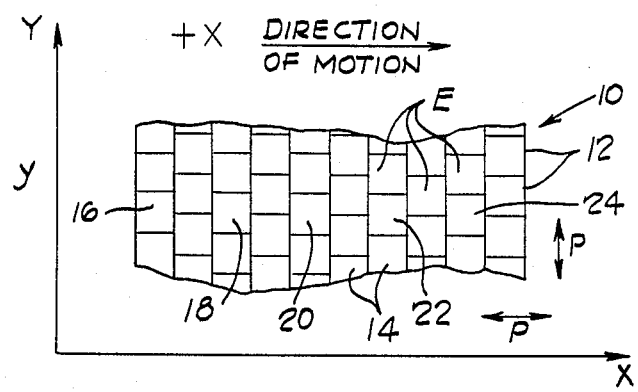
FIG. 5 is an elevational vie,, partially broken away, illustrating a portion of a component of the system illustrated in FIGS. 1 and 2.

Referring to FIG. 5, the detector matrix 10 of the present invention is represented as a staggered array of square detector elements arranged in horizontal rows such as indicated at 12 and vertical columns such as indicated at 14. Each column 14 is vertically displaced or offset from adjacent columns by a distance equal to one half p, i.e., one half the side dimension of each square detector element.

In this configuration, the modulation transfer function (MTF) is still given by the relation expressed in equations 2 and 3 above.

In the preferred embodiment, the radiation-sensitive square faces of the detector elements are approximately 0.35 millimeters on a side. The staggered detector array includes 30 columns and 2016 rows having an overall dimension of approximately 10.5 by 352.8 millimeters.

Each detector is of a known type, such as a photodiode coupled to an X-ray scintillator, which produces an analog charge signal in response to receipt of radiation incident on its sensitive surface. This charge is integrated during the time that the element's radiation sensitive face is exposed to the radiation.

Time delay and integrate circuitry is coupled to each row of detector elements. As the detector moves in the direction given by the arrow in FIG. 5 relative to the patient, the TDI circuitry samples, delays and adds charge in a unique sequence, to enable great improvement in resolution in conjunction with the staggered array of detector elements. Each accumulation step is preceded by a sampling step.

The Nyquist frequency is doubled in the y direction by staggering the detector elements. The Nyquist frequency is doubled in the x direction by sampling every detector half-width increment, in conjunction with use of the staggered array.

In the present embodiment, the sampling takes place at a frequency such that a sampling occurs with each successive incremental relative movement of the detector by a distance of p/2. That is, the time delay and integrate circuitry samples the charge packets present at the detector element outputs along a row each time the detector array has moved a distance equal to half the length of a side of one of the square detector elements.

Figure 6:
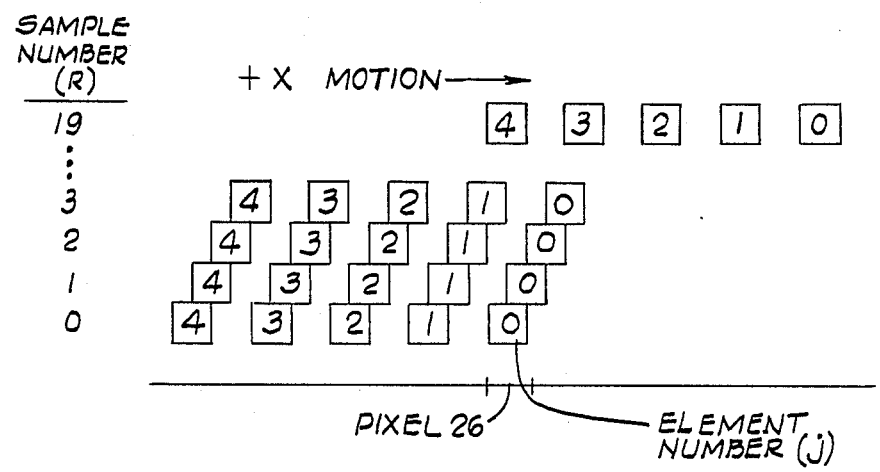
FIG. 6 is a graphical illustration of an operative sequence associated with the use of the component illustrated in FIG. 5.

The specific operation of the TDI circuitry will be discussed in connection with FIG. 6.

It is important to define the meaning of a "row" of detectors as illustrated in FIG. 5. A "row" of detector elements extending in the x direction as in FIG. 5 is exemplified by the set of elements 16, 18, 20, 22, 24 as illustrated in that figure. Thus, the center-to-center spacing of elements in a given row extending in the x direction is 2p, or twice the lateral dimension of a side of a single one of the uniform detector elements.

In the y direction as shown in FIG. 4, the sampling distance dictated by the staggered array geometry is p/2, because the rows are partially interspersed. This sampling distance yields a Nyquist sampling cutoff at $f = 1/p$, which is equal to the aperture cutoff frequency. Thus, in this preferred embodiment, the actual resolution obtainable in the y direction is now limited only by the aperture cutoff frequency, which, as described above, is twice as favorable as that dictated by the Nyquist spatial frequency which obtained in the prior art rectangular array system.

The same coincidence between the limiting resolution of the Nyquist frequency and that of the aperture cutoff is achieved in the x direction by choosing the sampling interval t in the x direction so that the sampling incremental distance of detector relative motion is p/2.

This improvement results because the Nyquist frequency doubles as the sampling distance is halved. For a sampling distance of p the Nyquist frequency $f_n = 1/(2p)$. When p is replaced with p/2, the expression becomes $f_n = 1/[2(p/2)]$, or $f_n = 1/p$.

Therefore, for a predetermined detector element size the configuration of the present embodiment provides twice the resolution, in both directions, of that of the prior art. Pixel size in the present embodiment is only one quarter of the area of one detector element.

Moreover, the embodiment of this invention substantially reduces aliasing, compared to that of the standard prior art rectangular array.

In order to achieve these improvements, the staggered detector array requires associated time delay and integrate circuitry that differs from the circuitry whose operation is exemplified in equation 1. Consider a single row of detector elements in FIG. 5 extending in the x direction, and comprising five elements. Let s(j,k) represent the k-th sample of the j-th element, where the elements are numbered from right to left and j ranges from 0 to 4 (see FIG. 6). Consider also the image portion or pixel which is designated by the reference character 26 and which is aligned with element 0 at sample 0. Since the sampling distance in this embodiment is p/2, this particular pixel will be aligned with element 1 only at the fourth sampling, with element 2 at sample 8, element 3 at sample 12 and so on. Therefore, the final value generated by the time delay and integration circuitry and corresponding to this pixel will be:

$$S_0 = s(0,0) + s(1,4) + \ldots + s(4,16). \tag{4a}$$

Analogous equations apply for other pixels which are aligned with element 0 at sample times 1, 2 and 3:

$$S_1 = \ldots + s(4,17). \tag{4b}$$

$$S_2 = s(0,2) + s(1,6) + \ldots + s(4,18) \tag{4c}$$

$$S_3 = s(0,3) + s(1,7) + \ldots + s(4,19). \tag{4d}$$

Figure 7:
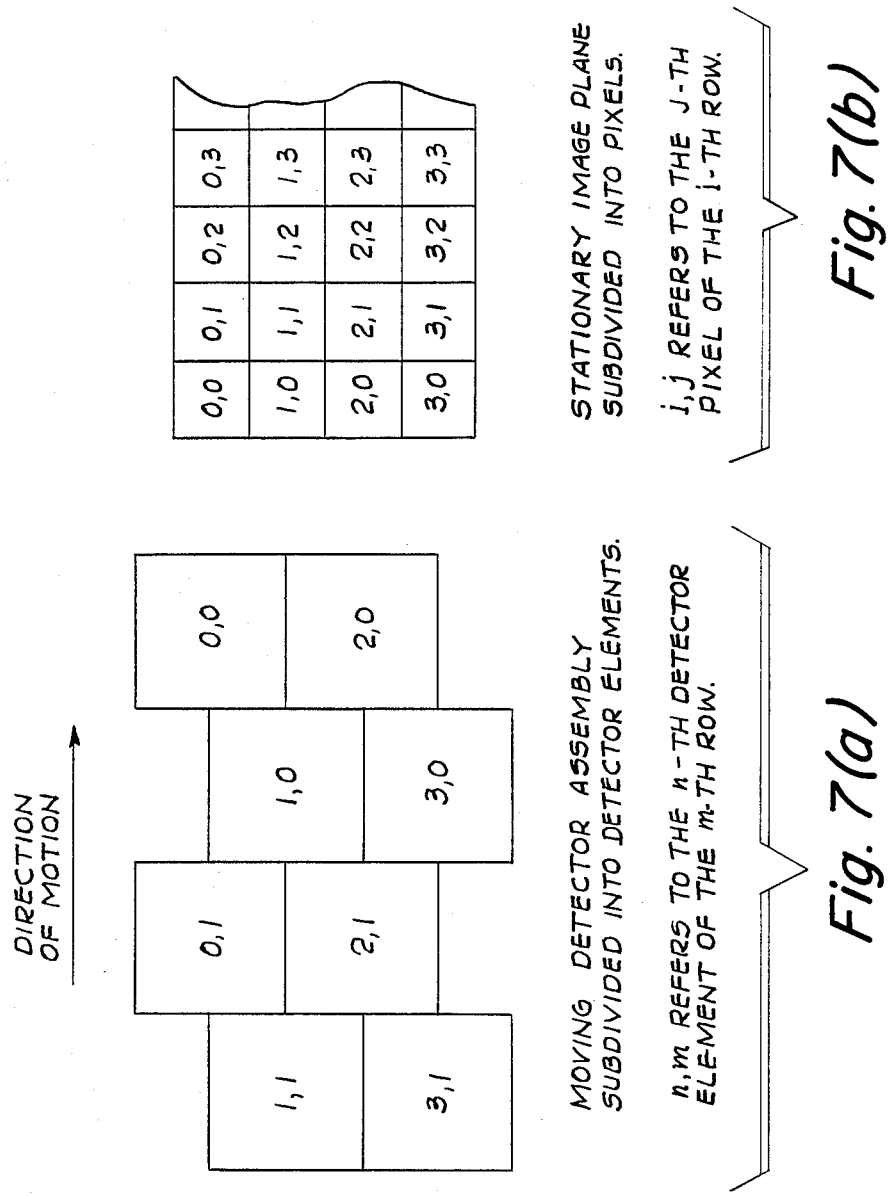
FIGS. 7(a) and 7(b) is a graphical illustration of a component of the system of FIGS. 1 and 2, illustrating a particular form of mathematical notation interpretive of a portion of the present disclosure.
Figure 8:
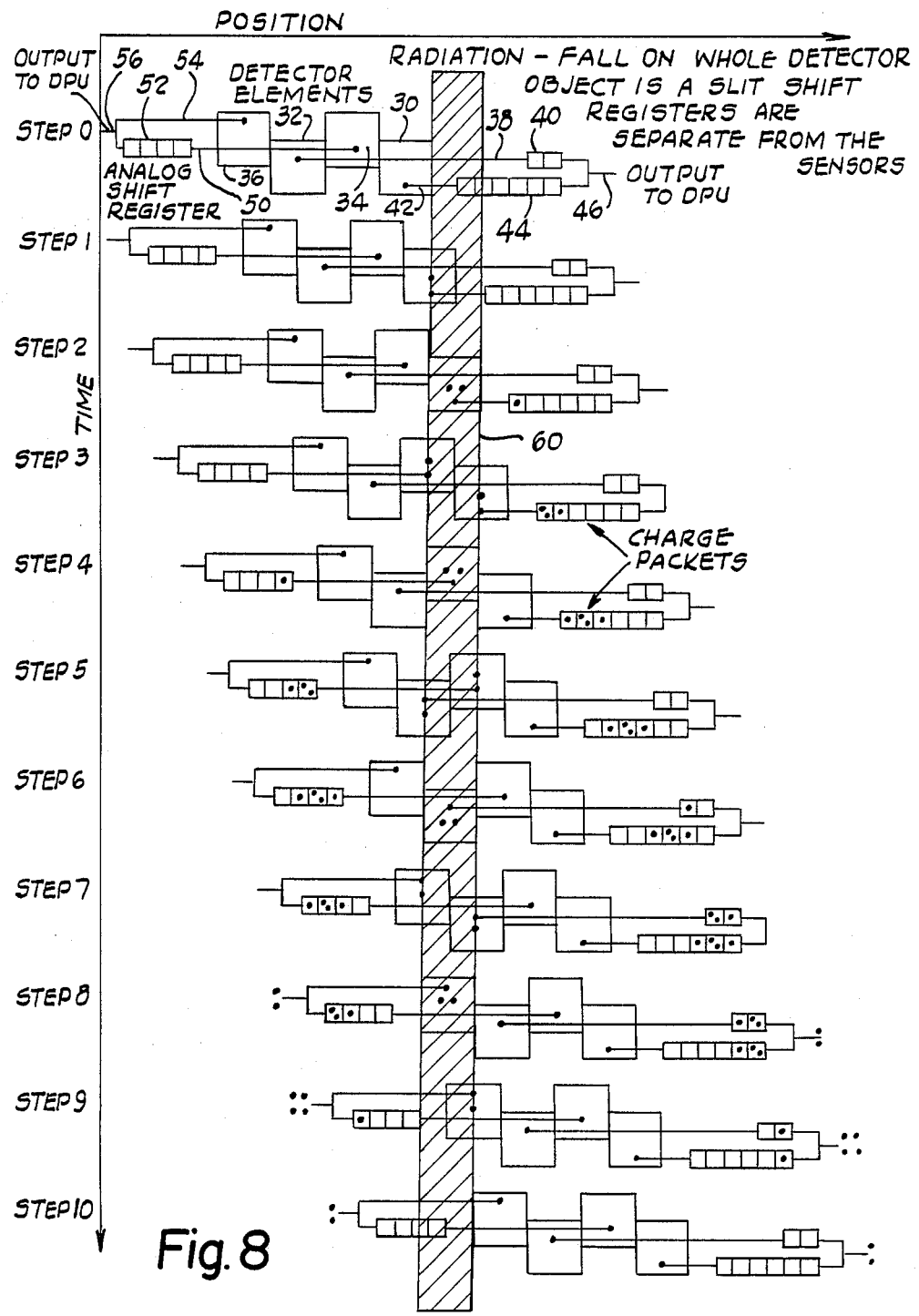
FIG. 8 is a geographical illustration showing a sequence of operation of components of the system of FIGS. 1 and 2, including the component illustrated in FIG. 5.

The shift and add sequence represented by equation 4 and FIGS. 7 and 8 can be implemented in a variety of ways. A preferred implementation involves the use of CCD analog shift registers in a time delay integration configuration. It is important to note, however, that operating in this sequence, the TDI CCD cells cannot themselves constitute a portion of the detector elements. Rather, the detector elements must be separate from, but coupled to, the TDI circuitry.

FIG. 8 illustrates the structure and operation of circuitry for implementing the time delay and integrate sequencing represented by equations 4 and 5. FIG. 8 illustrates a portion of a detector array at eleven different steps of relative detector motion with respect to a patient, these steps being labeled from 0–10.

As shown in the illustration corresponding to step 0, two rows of detector elements are illustrated, there being two detector elements in each row, having their center-to-center spacing equal to 2p, where p is the dimension of one side of each of the square elements. Referring to the illustration of step 0, one row of such elements is designated 30, 32, while the other row is designated 34, 36.

Detector element 32 is coupled by a lead 38 to a two-cell shift register 40. Detector element 30 is coupled by a lead 42 to a six element shift register 44. The outputs of the registers 40, 44 are connected in parallel to an output line 46. The output line 46 receives analog signals from the registers 40, 42 representing total charge value corresponding to a particular pixel or image portion which has been "read" by both of the detector elements 30, 32 in the detector element row of interest. Output lead 46 is coupled as an input to the ADC.

The analog output of detector element 34 is coupled by a lead 50 to a four-cell shift register 52. The output of detector element 36 is coupled by a lead 54 directly in parallel with the output of the shift register 52, the resultant output being summed and appearing at an output lead 56. Analog signals appearing at the lead 56 are transmitted to the DPU for further processing in accordance with known techniques. Each output appearing at the lead 56 is an analog signal representing a total pixel value of an image portion which has been read by both the detector elements in the associated row, i.e., elements 34, 36.

Each of the leads connected directly to elements 30, 32, 34, 36 comprises a translucent polysilicon conductor.

It is important to understand that the signals at the leads 46, 56 are not mixed by the system, because they are signals representing different rows of data in the total image, elements 34, 36 representing an upper row and elements 30, 32 representing a lower row.

Also illustrated in FIG. 8 is a shaded band of radiation 60. The radiation band 60 is to be considered as falling upon whatever detector element(s) are illustrated as within the band at any given step. In practice, radiation from the spread beam is continuously directed through a patient toward all of the detector elements simultaneously, the radiation falling upon individual detector elements in greater or lesser amounts depending on the patient's internal body structure. For purposes of clarity of illustration, however, the radiation pattern emergent from the patient will be considered to be a slit having a width equal to that of the radiation band 60 illustrated in FIG. 8.

Also for purposes of clarity, the reference characters illustrated in conjunction with the illustration corresponding to step 0 are omitted for the other steps, in order to avoid undue cluttering of the drawing. The reference characters associated with the illustration of step 0 are to be considered as applicable also to the corresponding portions of the illustrations of the subsequent steps 1–10.

The operation of the circuitry and apparatus in FIG. 7 is as follows.

At step 0, the radiation band 60 is not incident on any portion of any of the detector elements. Therefore, none of the detector elements generate any charge packets constituting analog signals representing incident radiation.

It is be understood that clocking circuitry, of known type but not illustrated specifically in FIG. 8, is provided. At each step increment, the clocking circuitry causes the signals at the leads 38, 42, 54 and 50 to be sampled. With respect to the leads 38, 42 and 50, which are coupled respectively to shift registers 40, 44, 52, the clocking circuitry causes a signal representing the respective charge packet from the associated element to be stored in the first cell of the corresponding shift register. The clocking signal also causes any previously stored charge related signals in each of the shift registers to shift to the next subsequent cell of that register. The clocking signal causes any signal stored in the ultimate cell of a shift register to proceed to the associated one of outputs 46, 56.

The clocking circuitry executes its ensemble of operation as described above with a frequency such that the elements are sampled at successive increments of p/2 detector travel.

In the portion of FIG. 8 designated step 1, the detector has moved to the right, relative to the patient, a distance of p/2, or half the width of a detector element. At this point the detector element 30 is positioned such that half the detector element receives incident radiation from the slit radiation pattern 60. The element 30 generates a charge "packet" which is designated by a dot located in the center of that element. The other elements, not being within the radiation slit 60, generate no charge packets.

By the time the detector portion has reached step 2 of its incremental motion, the charge packet represented by the dot in the illustration of step 1 has been clocked into the first cell of the register 44. The element 30 is now completely illuminated with incident radiation from the slit pattern 60. Since the detector element generates charge packets in accordance with the amount of radiation received, this element produces an amount of charge at its output equal to two of the packets designated by the dot in step 1. This generated charge is represented by two dots within element 30 as illustrated in connection with step 2.

Upon arrival at the location illustrated in connection with step 3, the double charge packet produced by element 30 is clocked into the first cell of the register 44. The single charge packet formerly located in the first cell of register 44 is clocked into the second cell of that register. Meanwhile, in a fashion analogous to that described above, both elements 30 and 34 generate single charge packets.

This progression of generation and storage of charge packets continues. Note that it is not until step 6 that any charge from the element 32, in the same row as element 30, is clocked into the two-cell register 40. It will be recalled that charge, in this illustration, was first clocked into the register 44 at step 2, four steps previous to the first appearance of charge signal in the register 40. Thus, charge clocked into the register 44 is delayed by four p/2 increments of relative detector motion, with respect to charge in the register 40.

It will also be seen from a review of equation 4 that the circuitry configuration and operating sequence of FIG. 8 implements the operations described in that equation. More specifically, the FIG. 8 configuration implements the operations described in those equations wherein signals from each element of a detector element row are combined with signals from the immediately following element in the row only after a delay of four sampling steps.

Accordingly, the operations described in equation 4 are implemented by providing each detector element in a row with a delay which is different and independent from the delay imposed on the outputs of other cells in the row. In this way, the prescribed delay sequences for implementing equations 4 and 5 can be built into the TDI circuitry coupled to the respective elements.

Referring again to FIG. 8, step 8, it will be seen that at this point sufficient steps have taken place such that the output of data to the DPU has begun. Step 8 corresponds to an output representing two charge packets at the lead 46. The signal corresponding to two charge packets is derived from the summation of the two single charge representing signals present in the ultimate cells of each of the shift registers 44, 40.

At step 9, the clocking circuitry produces an output representing four charge packets, the result of the summation of the two signals each representing two charge packets present in the ultimate cells of the registers 44, 40 at step 8.

As the signals representing an image pixel read by the elements 30, 32 are produced at the output 46, analogously produced signals are generated at the output 56 which corresponds to the upper row of elements, i.e., elements 34, 36.

A relative delay in output signals from the element 34, with respect to those from the element 36, is effected by the presence of the four-cell shift register 52 in the line 50, and by the fact that the output from the element 36 is presented directly over the lead 54 to the output 56.

It will be observed that, by the use of the TDI circuitry described in connection with FIG. 8, the signal-to-noise ratio of the output signals describing the respective image pixel is enhanced. If the TDI circuitry illustrated in FIG. 8 were not used, the output of, for example, element 30, in passing through the radiation slit 60 would be a succession of three signals representing 1, 2 and 1 charge packet, respectively, which would be emitted at steps 1, 2 and 3. By the use of TDI circuitry, in connection with which the image pixel is defined by the sum of responses of the respective elements reading or viewing the pixel, the corresponding outputs are signals representing 2, 4 and 2 charge packets, occuring at steps 8, 9 and 10.

Design of techniques for producing imaging data from sequentially occurring line-representing sets of data from a photodiode array, such as produced here, are within the scope of ordinary skill in the art, as evidenced by publications including U.S. Pat. No. 4,203,037, to Gur et al, and by the several patents and publications identified therein, which are all hereby incorporated by reference.

FIG. 8 constitutes an illustration of the operation and components of the TDI circuitry in a simplified environment, i.e., considering only two rows of two detector elements each. Those of skill in the art will easily be able to expand this illustration in an analogous fashion to the use of larger numbers of elements in each row, and to larger numbers of rows. For example, if three elements were employed in each row, the right hand element in FIG. 8 would have its output coupled to a ten-cell shift register. The middle element will be coupled to a six-cell register and the left hand, or third element would be coupled to a two-cell register. This configuration would maintain the respective delay relationships in summing signals from the respective elements as expressed in equations 4 and 5 above.

It is to be understood that the description of this embodiment of the invention is intended to be illustrative, rather than exhaustive, of the invention. Those of ordinary skill in the relevant art will be able to make certain additions, deletions and modifications to the described embodiment of the invention, without departing from the spirit or scope of the invention, as described in the following claims.

We claim:

1. A medical imaging digital radiography system comprising:
   (a) a radiation source;
   (b) a detector assembly comprising an array of more than two columns of detector elements, each column containing more than two elements, said elements being arranged in a staggered pattern, each element being capable of producing an electrical output signal in response to incident radiation;
   (c) structure for mounting the radiation source spaced from the detector array to define a patient examining space;
   (d) power means for actuating the source to direct radiation toward the detector array and through the patient space, and
   (e) circuitry coupled to the detector array for producing an image of a patient from radiation emergent from a patient and incident on the detector array said circuitry including means for imposing different degrees of delay on electrical output signals from different ones among said detector elements.

2. A medical imaging system comprising:
   (a) a radiation source;
   (b) a staggered detector array comprising at least two rows of uniform detector elements, each detector element responsive to radiation incident thereon for producing an electrical output signal indicative of said incident radiation;
   (c) means for mounting said source and said detector array spaced sufficiently from one another to accommodate a patient in a space therebetween;
   (d) mechanism for effecting a motion of said detector array relative to a patient when located in the patient space, in a direction substantially parallel to said row;
   (e) power means for actuating said radiation source to propagate radiation from the source and toward said detector array, said radiation passing through a portion of a patient's body when located at the patient space, and
   (f) time delay and integrate circuitry coupled to said detector elements for producing an image of internal patient body structure in response to said electrical signals produced by said detector elements, said circuitry comprising sampling circuitry for sampling said detector element electrical signals at successive increments of detector array scanning motion less than a distance equal to a dimension of one of said uniform detector elements extending in said scanning direction.

3. The system of claim 2, wherein:
said detector array comprises additional elements defining a plurality of columns of said detector elements perpendicular to said row and being arranged in a staggered pattern.

4. The system of claim 2, wherein said detector array comprises:
at least three columns of said detector elements.

5. The system of claim 3, wherein said detector array comprises:
at least three columns of said detector elements.

6. An imaging system comprising:
(a) a penetrative radiation source;
(b) a detector array including a plurality of detector elements arranged in a staggered pattern, each detector element being responsive to incident radiation to produce an electrical signal indicative of such radiation;
(c) apparatus for mounting said source and said detector array in a spaced relation to facilitate location of a subject therebetween;
(d) mechanism for effecting scanning movement of said detector array relative to a subject when so located;
(e) time delay and integrate circuitry coupled to said detector elements and responsive to said electrical signals to produce a representative of an image describing internal structure of a subject when located between said source and said detector array, said time delay and integrate circuitry including means for imposing different degrees of delay on said electrical signals from different ones among said detector elements, and
(f) power means for actuating said source to propagate radiation toward said detector array.

7. The system of claim 6, wherein said staggered pattern comprises a pattern of partially interspersed rows of said elements.

8. A medical imaging system comprising:
(a) a source of penetrative radiation;
(b) a detector array comprising a plurality of detector elements arranged in a staggered pattern, each detector element responsive to penetrative radiation incident thereon to produce an electrical signal indicative of such radiation;
(c) structure for locating said source and said detector array in a spaced relationship to define a patient space therebetween;
(d) power means for actuating said radiation source to propagate penetrative radiation toward said detector array and through a patient at the patient space, and
(e) time delay and integrate circuitry coupled to said detector elements and responsive to said electrical signals to produce a representation of an image of internal structure of a patient when at the patient space, said time delay and integrate circuitry including means for imposing different degrees of delay on said electrical signals from different ones among said detector elements.

9. A medical diagnostic digital radiography system comprising:

(a) an X-ray source;
(b) a staggered detector assembly comprising a plurality of uniform rectangular detector elements arranged in partially interspersed rows, each detector element being responsive to x-radiation incident thereon to produce an electrical signal indicative of such radiation;
(c) apparatus for supporting said X-ray source and detector assembly in a spaced relationship;
(d) power means for actuating the X-ray to propagate X-rays along a path from the source toward said detector;
(e) mechanism for effecting a scanning motion of said detector assembly relative to a subject when located in said path;
(f) time delay and integrate sampling and delay circuitry coupled to said detector elements for producing from said electrical signals a representation of internal subject structure, said time delay and integrate circuitry operating in a mode wherein the output signal of a given element as to a given image pixel is sampled only at successive increments of detector motion equal to detector motion over a distance equal to twice the width of a single detector.

10. The system of claim 9, wherein said time delay and integrate circuitry comprises circuitry for sampling the outputs of each element of a row at successive increments of detector motion equal to one half an individual element width.

11. The system of claim 10, wherein said time delay and integrate circuitry comprises circuitry for interposing delay on the output signal of each element, with respect to the output of the immediately preceding element, equal to the time required for the detector to move a distance equal to twice the width of a single detector element.

12. A medical imaging method utilizing a radiation detector assembly including a plurality of individual radiation sensitive detector elements arranged in a pattern of partially interspersed rows, said method comprising the steps of:
(a) directing penetrative radiation through a subject to emerge from the subject as a pattern of radiation incident on said detector assembly;
(b) effecting a scanning motion of said detector assembly within said radiation beam and relative to said subject;
(c) sampling output signals from said detector elements in a time delay and integrate mode, said sampling taking place at successive increments of detector motion less than the width of a single detector element, and
(d) processing said sampling signals to provide information representing an image of internal structure of the subject.

13. A method of imaging, utilizing a staggered detector array of uniformly sized elements, said method comprising:
(a) directing penetrative radiation through a subject to emerge therefrom incident on said detector array;
(b) effecting a scanning motion of the array relative to the subject, and
(c) performing a time delay and integrate function on outputs from the detector array, including sampling the outputs at scanning motion increments equal to less than a uniform dimension of each element taken along the direction of scanning motion.

14. The method of claim 13, wherein said sampling comprises sampling at successive increments of about half said dimension.

15. An imaging system comprising:
   (a) an penetrative radiation source;
   (b) a detector assembly comprising a staggered array of detector elements comprising at least two rows of uniform square elements having centers spaced by 2p, where p is the dimension of an element side;
   (c) means for effecting a scanning motion of the array parallel to said row;
   (d) time delay and integrate imaging circuitry coupled to the elements, said circuitry comprising:
      (i) means for sampling detector element outputs with each p/2 of successive scanning motion increment;
      (ii) means for accumulating, as a representation for a given image portion, a set of only each fourth sampling of each detector output, and
      (iii) means for accumulating as a representation for another given image portion, a different set of fourth samplings offset in time from said set.

16. A digital imaging system comprising:
   (a) a source of penetrative radiation;
   (b) a detector comprising a staggered array of detector elements spaced from the source and positioned to receive penetrative radiation for producing signals therefrom;
   (c) means cooperatively for scanning said staggered detector array along a scanning path in space;
   (d) circuit means coupled to said detector array for implementing time delay and integrate shifting and adding sequence with respect to signals produced by said detector elements during said scanning for Nyquist sampling said detector element-produced signals.

17. An imaging system comprising:
   (a) a staggered detector array of uniformly sized penetrative radiation responsive elements;
   (b) means for directing penetrative radiation through a subject to emerge therefrom incident on said detector element array;
   (c) means for effecting a scanning motion of array relative to the subject, and
   (d) circuitry for performing a time delay and integrate function on outputs from the detector, said circuitry including means for sampling the outputs at scanning motion increments equal to less than a uniform dimension of each element taken along the direction of scanning motion;
   means for producing an image from said sampled outputs.

18. The system of claim 17, wherein said sampling means comprises circuitry for effecting sampling at successive increments of detector motion equal to about half of said dimension.

19. The system of claim 17, wherein said sampling means comprises circuitry for sampling at successive increments of detector motion equal to an integral submultiple of said dimension.

20. A medical diagnostic digital radiography system comprising:
   (a) an X-ray source;
   (b) a staggered detector assembly comprising a plurality of detector elements of uniform geometry arranged in partially interspersed rows, each detector element being responsive to X-radiation incident thereon to produce an electrical output signal indicative of such radiation;
   (c) apparatus for supporting said X-ray source and detector assembly in a spaced relationship;
   (d) power means for actuating the X-ray source to propagate X-rays along a path from the source toward said detector;
   (e) mechanism for scanning said detector assembly relative to a subject when located in said path;
   (f) time delay and integrate sampling and delay circuitry coupled to said detector elements for producing from said electrical signals a representation image describing internal subject structure, said time delay and integrate circuitry comprising circuitry for imposing delay on the output signal of each element, with the respect to the output signal of the immediately preceding element in the same row, equal to the time required for the detector to move a distance equal to a nonunity integral multiple of the width of a signal detector element.

21. An imaging system comprising:
   (a) a penetrative radiation source;
   (b) detector array including a plurality of detector elements arranged in a staggered pattern, each detector element being responsive to incident radiation to produce an electrical output signal indicative of such radiation;
   (c) apparatus for mounting said source and detector array in a spaced relation to facilitate location of a subject therebetween;
   (d) mechanism for effecting scanning movement of said detector array relative to a subject when so located;
   (e) time delay and integrate circuitry coupled to said detector elements and responsive to said electrical signals to produce a representation image describing internal structure of a subject when located between said source and said detector array, said time delay and integrate circuitry including means for imposing different amounts of delay upon the electrical output signals from different ones of said detector elements, and
   (f) power means for actuating said source to propagate radiation toward said detector array.

22. A medical imaging system comprising:
   (a) a source of penetrative radiation;
   (b) a detector array comprising a plurality of detector elements arranged in a staggered pattern, each detector element responsive to penetrative radiation incident thereon to produce an electrical signal indicative of such radiation;
   (c) structure for locating said source and said detector array in a spaced relationship to define a patient space therebetween;
   (d) power means for actuating said radiation source to propagate penetrative radiation toward said detector array and through a patient at the patient space, and
   (e) time delay and integrate circuitry coupled to said detector elements and responsive to said electrical signals from said elements to produce a representation image describing internal structure of a patient when at the patient space, said circuitry comprising means for imposing different delays in the electrical signals produced by different ones of said detector elements.

23. A medical imaging method utilizing a radiation detector assembly including a staggered plurality of rows of individual rad sensitive detector elements comprising at least two rows, said method co the steps of:
(a) directing penetrative radiation through a subject to emerge from the subject as a pattern of radiation incident on said detector assembly;
(b) effecting a scanning motion of said detector assembly within said radiation beam and relative to said subject;
(c) sampling output signals from said detector elements in a time delay and integrate mode, said sampling taking place at successive increments of detector motion less than the width of a single detector element, and comprising scanning said detector assembly in a direction substantially parallel to said rows of detector elements, said time delay and integrate mode sampling step further comprising:
  (i) sampling said detector element output signals at successive increments of detector motion equal to approximately one-half the width dimension of an individual detector element taken parallel to one of said rows;
  (ii) delaying respective output signals from detector elements of one of said rows in different amounts on order to present said output signals of said elements of said one of rows pertaining to a single image pixel simultaneously at an output;
  (iii) summing said simultaneously presented output signals;
(d) processing said summed signals to obtain representation of an image of internal subject structure.

24. A detector assembly for use in imaging penetrative radiation, said assembly comprising:
(a) a staggered array of detector elements, each element being responsive to incident radiation to produce an electrical signal indicative of said radiation, and
(b) time delay and integrate circuitry coupled to said detector elements for producing from said electrical signals a representation of an image of said incident radiation, said time delay and integrate circuitry comprising means for imposing different degrees of delay on said electrical output signals from different ones among said detector elements.

25. A medical imaging system comprising:
(a) a radiation detector assembly including a plurality of individual radiation sensitive detector elements, said elements having substantially uniform geometry and arranged in a staggered pattern of rows;
(b) means for directing penetrative radiation through a subject to emerge from the subject as a pattern of radiation incident on said detector assembly;
(c) means for effecting a scanning motion of said detector assembly relative to said subject in a direction substantially parallel to said rows of elements;
(d) means for sampling output signals from said detector elements at successive increments of detector motion;
(e) means for storing said sampling outputs;
(f) means for delaying respective output signals from detector elements of one of said rows in different amounts in order to present said output signals of said elements of said row, pertaining to a single image pixel, simultaneously at an output;
(g) means for summing said simultaneously presented output signals, and
(h) processing said summed signals to obtain presentation of an image of internal subject structure.

26. The system of claim 25, wherein:
(a) said delaying means comprises analog shift registers having differing numbers of cells, and clocking means for clocking said shift registers in synchronism with said sampling operation.

27. A medical imaging method utilizing a radiation detector assembly including a plurality of individual radiation sensitive detector elements arranged in a staggered pattern of partially interspersed rows, said method comprising the steps of:
(a) directing penetrative radiation through a subject to emerge from the subject as a pattern of radiation incident on said detector assembly;
(b) effecting a scanning motion of said detector assembly within said radiation beam and relative to said subject in a direction substantially parallel to said row of detector elements;
(c) sampling output signals from said detector elements in a time delay and integrate mode, said sampling taking place at successive increments of detector motion less than the width of a single detector element, said sampling comprising:
  (i) sampling said detector element output signals at successive increments of detector motion equal to approximately ½ the width dimension of an individual detector element parallel to one of said rows, and
  (ii) delaying respective output signals from detector elements of one of said rows in different amounts in order to present said output signals of said elements of said one of said rows pertaining to a single image pixel simultaneously at an output;
  (iii) summing said simultaneously presented output signals;
(d) processing said sampled signals to provide information representing an image of internal structure of the subject.

28. A medical imaging method utilizing a radiation detector assembly comprising an array of uniform radiation sensitive detector elements arranged in a staggered pattern of partially interspersed rows, said method comprising the steps of:
(a) directing penetrative radiation through a subject to emerge from the subject as a pattern of radiation incident on said detector assembly;
(b) effecting a scanning motion of said detector assembly within said radiation beams and relative to said subject, said scanning step comprising scanning said detector assembly in a direction substantially parallel to said row of detector elements;
(c) sampling output signals from said detector elements in a time delay and integrate mode, said sampling taking place at scanning intervals of detector motion less than the width of a single detector element, said time delay and integrate mode sampling step further comprising:
  (i) sampling said detector element output signals at successive increments of detector motion equal to approximately one-half the width dimension of an individual detector element taken parallel to one of said rows, and
  (ii) delaying respective output signals from detector elements of one of said rows in different amounts in order to present said output signals of said elements of said row pertaining to a single image pixel simultaneously at an output;
  (iii) summing said simultaneously presented output signals;
(d) processing said sampled and summed signals to provide information representing an image of internal structure of the subject.

* * * * *